US006703533B1

(12) United States Patent
Belen'Kii et al.

(10) Patent No.: US 6,703,533 B1
(45) Date of Patent: Mar. 9, 2004

(54) PREPARATION OF SELECTED FLUOROOLEFINS

(75) Inventors: Gennadii Gerskovich Belen'Kii, Moscow (RU); Viacheslav Alexandrovich Petrov, Hockessin, DE (US); Sergei Arnol'Dovich Postovoi, Moscow (RU); Paul Raphael Resnick, Cary, NC (US); Yurii Vilovich Zeifman, Moscow (RU)

(73) Assignee: E. I. du Pont de Nemours and Company, Wilmington, DE (US)

( * ) Notice: Subject to any disclaimer, the term of this patent is extended or adjusted under 35 U.S.C. 154(b) by 658 days.

(21) Appl. No.: 09/979,783

(22) PCT Filed: Aug. 17, 2000

(86) PCT No.: PCT/US00/22530

§ 371 (c)(1),
(2), (4) Date: Nov. 21, 2001

(87) PCT Pub. No.: WO01/14294

PCT Pub. Date: Mar. 1, 2001

(30) Foreign Application Priority Data

Aug. 20, 1999 (RU) ............................................. 99118168

(51) Int. Cl.⁷ .................... C07C 17/00; C07C 17/25; C07C 19/08; C07C 21/18
(52) U.S. Cl. ....................... 570/156; 570/136
(58) Field of Search ................................. 570/123, 124, 570/127, 128, 134, 135, 136, 143, 144, 153, 155, 156

(56) References Cited

U.S. PATENT DOCUMENTS

| 3,192,274 A | 6/1965 | Baranaucksa et al. |
| 4,705,904 A | 11/1987 | Bonfield et al. |
| 4,766,238 A | 8/1988 | Furutaka et al. |
| 4,820,884 A | 4/1989 | Weigert |
| 5,043,491 A | 8/1991 | Webster et al. |
| 5,536,885 A | 7/1996 | Hung et al. |

FOREIGN PATENT DOCUMENTS

| EP | 0 434 407 A1 | 6/1991 |
| WO | WO 9842645 | 10/1998 |

OTHER PUBLICATIONS

Middleton, William J. et al.; "1–Trifluoromethyl–1,2, 2–triphenylethylenes. Synthesis and postcoital antifertility activity", J. Med. Chem. (1971), 14(12), 1193–7, XP002156406 scheme IV, table IV.

*Primary Examiner*—Johann Richter
*Assistant Examiner*—Elvis O. Price

(57) ABSTRACT

A process is disclosed for producing $(CF_3)_2C=CH_2$, $CF_3CH=CF_2$, $CF_2=C(CF_3)OCF_2CHF_2$ and $C_6H_5C(CF_3)=CF_2$. The process involves contacting the corresponding fluorocarbon starting material selected from $(CF_3)_2CFCH_2F$, $(CF_3)_2CHF$, $(CF_3)_2CFOCF_2CHF_2$ and $C_6H_5CF(CF_3)_2$, in the vapor phase, with a defluorination reagent selected from carbon, copper, iron nickel and zinc at an elevated temperature of at least 300 °C.

2 Claims, No Drawings

PREPARATION OF SELECTED FLUOROOLEFINS

This application represents a national filing under 35 USC 371 of International Application No. PCT/US00/22530 filed Aug. 17, 2000, and claims priority of Russian Application No. 99118168 filed Aug. 20, 1999.

FIELD OF THE INVENTION

This inventions concerns a process for the manufacture of certain fluorocarbons which have an olefinic bond by defluorination of a fluorocarbon starting material having a corresponding saturated bond.

BACKGROUND

Fluorinated olefins are used to prepare fluoropolymers. These polymers typically have a unique combination of properties. These include inter alia high thermal stability, chemical inertness, unusual surface properties, low dielectric constant and low flammability.

2-Trifluoromethyl-3,3,3-trifluoropropene (i.e., $(CF_3)_2C=CH_2$ or HFIB) is an example of a fluoroolefin that has been used to prepare various polymers. For example, it has been copolymerized with vinylidene fluoride to produce an alternating copolymer having exceptional thermal, chemical and mechanical properties. Numerous routes to HFIB have been disclosed. For example, U.S. Pat. No. 4,705,904 discloses the manufacture of HFIB by reacting hexafluoroacetone or hexafluoropropylene oxide, its precursor, with ketene or a ketene precursor at 500° C. to 700° C. Traces of perfluoroisobutylene, a highly toxic olefin, are found in the crude product mixture. U.S. Pat. No. 4,766,238 discloses a process for the preparation of HFIB by the reaction of monochloromethyl 2-trifluoromethyl-3,3,3-trifluoropropionate with an amine. The propionate ester is prepared by chlorination of the methyl ester. The use of chlorine or chlorine-containing precursors presents a waste disposal problem. Further disadvantages of the art processes are described in U.S. Pat. No. 4,705,904.

U.S. Pat. No. 4,820,884 discloses a process for preparing an unsaturated aliphatic or cycloaliphatic perfluorocarbon having at least six carbon atoms and having at least one carbon-carbon double bond comprising contacting the corresponding perfluoroalkane or perfluorocycloalkane having at least two adjacent tertiary carbon atoms with activated carbon at a temperature of from about 300° C. to about 500° C.

There is an interest in developing more efficient processes for the manufacture of unsaturated fluorocarbons, particularly, fluorinated olefins. Furthermore, the unsaturated fluorocarbons prepared by the process of this invention also contain hydrogen. These compounds, unlike perfluorinated unsaturated fluorocarbons, pose less of an environmental problem and are typically less expensive than their perfluorinated analogues.

SUMMARY OF THE INVENTION

A process is provided for producing an olefinic fluorocarbon selected from the group consisting of $(CF_3)_2C=CH_2$, $CF_3CH=CF_2$, $CF_2=C(CF_3)OCF_2CHF_2$ and $C_6H_5C(CF_3)=CF_2$. The process comprises contacting the corresponding fluorocarbon starting material selected from the group consisting of $(CF_3)_2CFCH_2F$, $(CF_3)_2CHF$, $(CF_3)_2CFOCF_2CHF_2$ and $C_6H_5CF(CF_3)_2$, in the vapor phase, with a defluorination reagent selected from the group consisting of carbon, copper, iron, nickel and zinc at an elevated temperature of at least 300° C.

DETAILED DESCRIPTION

In accordance with the process of this invention, certain hydrogen-containing fluorocarbon starting materials surprisingly defluorinate (i.e., lose two fluorine atoms) rather than dehydrofluorinate (i.e., lose hydrogen fluoride). In particular, it has been found that $(CF_3)_2C=CH_2$ can be produced from $(CF_3)_2CFCH_2F$; $CF_3CH=CF_2$ can be produced from $(CF_3)_2CHF$; $CF_2=C(CF_3)OCF_2CHF_2$ can be produced from $(CF_3)_2CFOCF_2CHF_2$; and

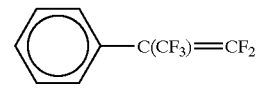

can be produced from

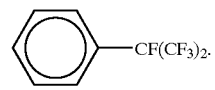

$(CF_3)_2CFCH_2F$ can be prepared by the reaction of difluoromethane, antimony pentafluoride and perfluoropropylene in an autoclave at 80° C. Further details are described in International Publication No. WO 98/42645. $(CF_3)_2CHF$ (227ea) can be prepared by the addition of HF to hexafluoropropene in the presence of activated carbon as described in British Patent Specification No. 902,590. $(CF_3)_2CFOCF_2CHF_2$ is a known compound (see Example 7). $C_6H_5CF(CF_3)_2$ can be prepared by a procedure described in W. A. Sheppard, J. Am. Chem. Soc., 87, 2410 (1965).

The carbon defluorination reagent includes activated carbon and acid-washed carbons (e.g., carbons which have been treated with hydrochloric acid or hydrochloric acid followed by hydrofluoric acid). Suitable acid treatment of carbons is described in U.S. Pat. No. 5,136,113. The carbon catalyst also includes three dimensional matrix porous carbonaceous materials. Examples are those described in U.S. Pat. No. 4,978,649. Of note are three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

The carbon, copper, iron, nickel and zinc defluorination reagents can be in any convenient form such as powder, granules and chips. The iron and nickel reagents may also be in gauze form. The metal defluorination reagents (i.e., Cu, Fe, Ni and Zn) can be regenerated by reaction with hydrogen at temperatures of 300° C. to 600° C.

In the process of the invention a fluorocarbon starting material selected from $(CF_3)_2CFCH_2F$, $(CF_3)_2CHF$, $(CF_3)_2CFOCF_2CHF_2$ and $C_6H_5CF(CF_3)_2$ is contacted with the defluorination reagent at a temperature of from about 300° C. to about 800° C., preferably from about 350° C. to about 500° C. The fluorocarbon starting material is reacted in the vapor phase and may be contacted with the defluorination reagent neat or diluted with an inert gas such as argon and nitrogen.

The contact time is typically from about 0.1 seconds to about 30 minutes.

The vapor phase process of this invention can be carried out using well-known chemical engineering practice. The process is conveniently done at atmospheric pressure, although subatmospheric or superatmospheric pressures can be employed. Reactor vessels of stainless steel are typically used although other materials such as nickel-based corrosion resistant alloys such as Hastelloy™ nickel alloy can be used.

Without further elaboration, it is believed that one skilled in the art can, using the description herein, utilize the present invention to its fullest extent. The following specific embodiments are to be construed as illustrative, and not as constraining the remainder of the disclosure in any way whatsoever.

EXAMPLES

| Legend | |
| --- | --- |
| 338 myq is $(CF_3)_2CFCH_2F$ | HFIB is $(CF_3)_2C=CH_2$ |
| 227 ea is $(CF_3)_2CHF$ | 1225 zc is $CF_3CH=CF_2$ |

The reactor used for all the examples was a stainless steel tube 510 mm long×14 mm diameter; the operating zone was 360 mm.

Example 1

$(CF_3)_2CFCH_2F \rightarrow (CF_3)_2C=CH_2$

Iron filings (70 g) were placed in the steel tube. Hydrogen was passed over the iron filings for 3 hours at 500° C. The hydrogen flow was stopped and $(CF_3)_2CFCH_2F$ (338myq, 5 g) in argon was passed through the tube for 2.5 hours. The reactor products were condensed in a trap (−78° C.) and a mixture (4.5 g) containing $(CF_3)_2C=CH_2$ (hexafluoro-isobutene or HFIB, 22%) and $(CF_3)_2CFCH_2F$ (78%) as determined by gas chromatography and $^{19}F$ NMR was found. The yield of HFIB was 67% and the conversion of 338myq was 30%.

Example 2

$(CF_3)_2CFCH_2F \rightarrow (CF_3)_2C=CH_2$

Activated carbon (22 g) was placed in the steel tube. 338myq (5 g) in argon was passed through the tube at 350° C. for 5 hours. The reactor products were condensed in a trap (−78° C.) and a mixture (4.5 g) containing HFIB (34%) and 338myq (66%) as determined by gas chromatography, mass spectroscopy, $^1H$ NMR and $^{19}F$ NMR was found. The yield of HFIB was 57%.

The reaction was repeated at 450° C. The reactor products contained HFIB (87%) and 338myq (13%) as determined by gas chromatography, mass spectroscopy, $^1H$ NMR and $^{19}F$ NMR. The yield of HFIB was 67%.

Example 3

$(CF_3)_2CFCH_2F \rightarrow (CF_3)_2C=CH_2$

Nickel chips (37 g) were placed in the steel tube. 338myq (6.2 g) in argon was passed through the tube at 500° C. for 2 hours. The reactor products were condensed in a trap (−78° C.) and a mixture (5.8 g) containing HFIB (6.3%) and 338myq (93.7%) was found. The yield of HFIB was 57% and the 338myq conversion was 13%.

Example 4

$(CF_3)_2CFCH_2F \rightarrow (CF_3)_2C=CH_2$

Zinc chips (72 g) were placed in the steel tube. 338myq (7.5 g) in argon was passed through the tube at 500° C. for 2 hours. The reactor products were condensed in a trap (−78° C.) and a mixture (6 g) containing HFIB (12%) and 338myq (88%) was found. The yield of HFIB was 72% and the 338myq conversion was 16%.

Example 5

$(CF_3)_2CFCH_2F \rightarrow (CF_3)_2C=CH_2$

Copper chips (54 g) were placed in the steel tube. 338myq (5 g) in argon was passed through the tube at 500° C. for 2 hours. The reactor products were condensed in a trap (−78° C.) and a mixture (4.5 g) containing HFIB (10%) and 338myq (90%) was found. The yield of HFIB was 58% and the 338myq conversion was 15.4%.

Example 6

$(CF_3)_2CHF \rightarrow CF_3CH=CF_2$

Iron filings (80 g) were placed in the steel tube. 227ea (10 g) was passed through the tube at 500° C. for 4 hours. The reactor products were condensed in a trap (−78° C.) and a mixture (6.1 g) containing 1225zc (9.5%) and 227ea (90.5%) was found. The yield of 1225zc was 16% and the 227ea conversion was 55%.

Comparative Example A

Preparation of $CF_3CF_2CH_2F$ $CF_3CF_2CH_2F$ can be prepared by the reaction of difluoromethane, antimony pentafluoride and tetrafluoroethylene in an autoclave at 50° C. Further details are described in International Publication No. WO 98/42645.

$CF_3CF_2CH_2F$ did not react when contacted with either iron filings or carbon under the same conditions as described in Example 6.

Example 7

$(CF_3)_2CFOCF_2CHF_2 \rightarrow CF_2=C(CF_3)OCF_2CHF_2$

Preparation of $(CF_3)_2CFOCF_2CHF_2$

A solution of $(CF_3)_2CFOCF_2CF_2I$ (21.3 g) in isopropanol (8 mL) was added dropwise to a suspension of Al chips (1 g) and $HgCl_2$ (0.4 g) in isopropanol (30 mL). After the exothermic reaction was completed, the reaction mixture was stirred for 1 hour at 55° C. The reaction mixture was then distilled and a fraction with a b.p. of less then 80° C. was collected. This fraction was washed with an aqueous HCl solution and then distilled over conc. $H_2SO_4$ to give $(CF_3)_2CFOCF_2CHF_2$ (11.8 g, 80% yield), b.p. 44 to 46° C. The $^1H$ and $^{19}F$ NMR were in accord with the assigned structure:

Iron chips (70 g) were placed in the steel tube and activated with hydrogen at 500° C. $(CF_3)_2CFOCF_2CHF_2$ (4.6 g) in argon was passed through the tube at 500°. The reactor products were condensed in a trap (−78° C.) and a mixture (3.9 g) containing $(CF_3)_2CFOCF_2CHF_2$ (96.7%) and $CF_2=C(CF_3)OCF_2CHF_2$ (3.3%) was found. The yield of $CF_2=C(CF_3)OCF_2CHF_2$ was 18%.

Comparative Example B $C_3F_7OCHFCF_3$ did not react when contacted with either iron filings or carbon under the same conditions as described in Example 6.

Comparative Example C $(CF_3)_2CFOC_2H_5 \rightarrow (CF_3)_2C=O+C_2H_5F$ $(CF_3)_2CFOC_2H_5$ was prepared by the method described in French Patent Publication No. 1,508,638 (1967); Chem. Abstr. 70:1122a.

$(CF_3)_2CFOC_2H_5$ did not defluorinate when contacted with iron filings under the same conditions as described in Example 6. The ether decomposed to hexafluoroacetone and ethyl fluoride even at temperatures as low as 200° C.

Comparative Example D $(CF_3)_2CFCH_2CH_3 \rightarrow (CF_3)_2C=CH_2 + CF_2=C(CF_3)C_2H_5 + (CF_3)_2C=CHCH_3 + (CF_3)_2CHC_2H_5$ Preparation of $(CF_3)_2CFCH_2CH_3$ A mixture of perfluoroisopropyl iodide (5.6 g, 0.19 mole), ethylene (5 L, 0.2 mole) and benzoyl peroxide (3.2 g) was heated in a 100 mL steel autoclave at 100° C. for 6 hours with stirring. The reaction product contained perfluoroisopropyl,iodide and $(CF_3)_2CFCH_2CH_2I$ in a 1:1 ratio. Distillation of the reaction mixture gave $(CF_3)_2CFCH_2CH_2I$ (b.p. 118 to 124° C.) in 33% yield. $(CF_3)_2CFCH_2CH_2I$ (10 g) was added dropwise to a mixture of zinc dust (5 g) and acetic acid (30 mL). After the exothermic reaction was completed, the reaction mixture was stirred for 2.5 hours at 60° C., diluted with water and distilled to collect a fraction with a b.p. less than 100° C. The distillate was separated from water, dried over calcium chloride, and redistilled to give $(CF_3)_2CFCH_2CH_3$ (b.p. 39 to 42° C., 56% yield). The $^1H$ and $^{19}F$ NMR were in accord with the assigned structure.

Iron chips (70 g) were placed in the steel tube and activated with hydrogen at 500° C. $(CF_3)_2CFCH_2CH_3$ (3.8 g) in argon was passed through the tube at 500°. The reactor products were condensed in a trap (−78° C.) and a mixture (1.5 g) containing $(CF_3)_2CFCH_2CH_3$ (75%) and $(CF_3)_2C=CH_2$ (25%) was found. The yield of $(CF_3)_2C=CH_2$ was 17.3%. Traces of $CF_2=C(CF_3)C_2H_5$, $(CF_3)_2C=CHCH_3$ and $(CF_3)_2CHC_2H_5$ were also found.

Example 8

$C_6H_5CF(CF_3)_2 \rightarrow C_6H_5C(CF_3)=CF_2 + C_6H_5CH(CF_3)_2$

Iron chips (60 g) were placed in the steel tube, heated in argon for 4 hours and then activated with hydrogen at 500° C. for 1.5 hours. $C_6H_5CF(CF_3)_2$ (3.6 g) in argon was passed through the tube at 500°. The reactor products were condensed in a trap (−78° C.) and a mixture (1.5 g) containing $C_6H_5CF(CF_3)_2$ (79%), $C_6H_5C(CF_3)=CF_2$ (14%) and $C_6H_5CH(CF_3)_2$ (7%) was found. The yield of $C_6H_5C(CF_3)=CF_2$ was 11% and the conversion of $C_6H_5CF(CF_3)_2$ was 67%.

What is claimed is:

1. A process for producing an olefinic fluorocarbon selected from the group consisting of $(CF_3)_2C=CH_2$, $CF_3CH=CF_2$, $CF_2=C(CF_3)OCF_2CHF_2$ and $C_6H_5C(CF_3)=CF_2$, comprising:

contacting the corresponding fluorocarbon starting material selected from the group consisting of $(CF_3)_2CFCH_2F$, $(CF_3)_2CHF$, $(CF_3)_2CFOCF_2CHF_2$ and $C_6H_5CF(CF_3)_2$, in the vapor phase, with a defluorination reagent selected from the group consisting of carbon, copper, iron, nickel and zinc at an elevated temperature of at least 300° C.

2. The process of claim 1 wherein $(CF_3)_2C=CH_2$ is produced from $(CF_3)_2CFCH_2F$.

* * * * *